(12) United States Patent
Urban et al.

(10) Patent No.: US 9,315,445 B2
(45) Date of Patent: *Apr. 19, 2016

(54) PHOTOREACTIVE MONOMERS

(71) Applicant: BASF SE, Ludwigshafen (DE)

(72) Inventors: Dieter Urban, Speyer (DE); Ulrike Licht, Mannheim (DE); Christopher Barner-Kowollik, Stutensee-Blankenloch (DE); Guillaume Delaittre, Mannheim (DE); Elena Frick, Karlsruhe (DE)

(73) Assignee: BASF SE, Ludwigshafen (DE)

( * ) Notice: Subject to any disclaimer, the term of this patent is extended or adjusted under 35 U.S.C. 154(b) by 9 days.

This patent is subject to a terminal disclaimer.

(21) Appl. No.: 14/021,040

(22) Filed: Sep. 9, 2013

(65) Prior Publication Data

US 2014/0073810 A1     Mar. 13, 2014

Related U.S. Application Data

(60) Provisional application No. 61/699,897, filed on Sep. 12, 2012.

(51) Int. Cl.
| | | |
|---|---|---|
| *C07C 69/54* | (2006.01) | |
| *C07C 67/14* | (2006.01) | |
| *C07C 67/28* | (2006.01) | |
| *C07C 67/29* | (2006.01) | |
| *C07C 45/64* | (2006.01) | |

(52) U.S. Cl.
CPC ............... *C07C 69/54* (2013.01); *C07C 45/64* (2013.01); *C07C 67/14* (2013.01); *C07C 67/28* (2013.01); *C07C 67/29* (2013.01)

(58) Field of Classification Search
CPC ........ C07C 67/28; C07C 67/29; C07C 69/54; C07C 303/08
See application file for complete search history.

(56) References Cited

FOREIGN PATENT DOCUMENTS

DE     693 21 830 T2     3/1999

OTHER PUBLICATIONS

Winkler et al, Macromolecules, Highly Orthogonal Functionalization of ADMET Polymers via Photo-Induced Diels-Alder Reactions, 2012, 45, pp. 5012-5019.*
Zaragoza Dorwald, Side Reactions in Organic Synthesis, 2005, WILEY-VCH Verlag GmbH & Co. KGaA, Weinheim, Preface. p. IX.*
Uji-Ie et al, Chemistry Letters, Photoenolization of 2-methylbenzophenone, 1977, pp. 499-502.*
Atonucci, Journal of Dental Research, Aldehyde Methacrylates Derived from Hydroxybenzaldehydes, 1978, 57(3), pp. 500-505, Abstract only.*

* cited by examiner

*Primary Examiner* — Paul A Zucker
(74) *Attorney, Agent, or Firm* — Oblon, McClelland, Maier & Neustadt, L.L.P.

(57) ABSTRACT

Photoreactive monomer which has (i) at least one free-radically polymerizable C—C double bond, (ii) at least one hydrophilic group selected from an ethylene glycol group and a polyethylene glycol group having at least 2 ethylene glycol units and (iii) at least one photoreactive group, the photoreactive group being a photoenolizable carbonyl group, and also a method for preparing the photoreactive monomers.

4 Claims, 1 Drawing Sheet

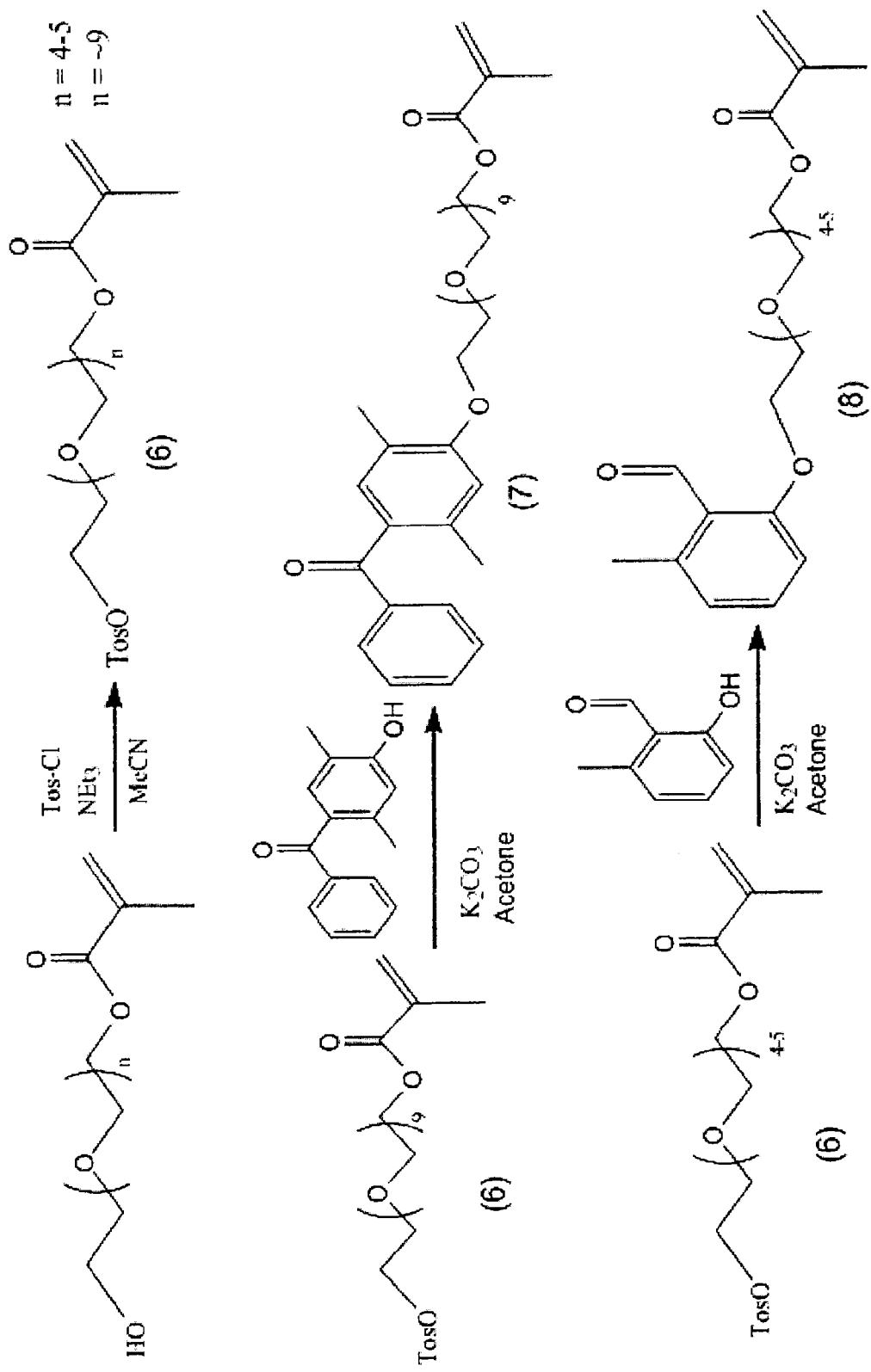

PHOTOREACTIVE MONOMERS

The present invention relates to a photoreactive monomer which has at least one free-radically polymerizable C—C double bond, at least one specified hydrophilic group and at least one photo-reactive group, and also a method for preparing the photoreactive monomer.

Photoreactive monomers are used for preparing aqueous polymer dispersions, from which polymer films are formed. To achieve the necessary and desired performance properties, such films often must be cross-linked so that an interparticulate cross-linking reaction between the polymer particles takes place. For this purpose, photoreactive monomers are used, which are reacted in an emulsion polymerization such that they are located on the particle surface. The film is then generally formed by uniform drying at room temperature in air. Subsequently the cross-linking is effected by the action of light.

In principle, functional specialty monomers for cross-linking aqueous polymer dispersions or polymers are known. These provide, in addition to the polymerizable group, further chemical moieties which can react with each other or with other groups. Most of the known monomers however are either difficult to use in aqueous polymer emulsions or solutions, due to their poor water solubility, or their other functional group requires high temperatures in order to react.

Accordingly, it was the object of the present invention to find new functional specialty monomers which afford controllable reactivity, if at all possible at room temperature, and good water solubility.

This object was achieved by photoreactive monomers which have
(i) at least one free-radically polymerizable C—C double bond,
(ii) at least one hydrophilic group selected from an ethylene glycol group and polyethylene glycol group having at least 2 ethylene glycol units and
(iii) at least one photoreactive group, the photoreactive group being a photoenolizable carbonyl group.

The invention also provides a method for preparing photoreactive monomers.

BRIEF DESCRIPTION OF THE DRAWING

FIG. 1: Synthetic scheme for preparing the photoreactive monomers of the present invention.

In the following, the term (meth)acrylate and related terms are used as shorthand for "acrylate or methacrylate".

The term "photoreactive" relates to compounds which can initiate photoinduced chemical reactions, i.e. their chemical reactivity is increased by exposure to light.

The photoreactive monomers have at least one, preferably only one, free-radically polymerizable C—C double bond. Particularly suitable examples are monomers in which the free-radically polymerizable C—C double bond is part of an acrylate or methacrylate group.

The photoreactive monomers additionally have at least one hydrophilic group. The effect of the hydrophilic group is that, in polymer dispersions, the spatially adjacent photoreactive group is located, together with the hydrophilic group, on the surface of dispersed polymer particles and is thus available for photoinduced reactions with compounds which are in the aqueous phase or which are sited on the surface of another polymer particle.

The hydrophilic group is a group having one or more ethylene glycol groups, e.g. 2 to 30, preferably 3 to 30 or 3 to 20, particularly 4 to 20 or 4 to 10 ethylene glycol groups. If the rest of the monomer has relatively high proportions of hydrophobic structural elements, then more ethylene glycol groups are preferably used, e.g. at least 5 to 20 or more. If the rest of the monomer has only low proportions of hydrophobic structural elements, then fewer ethylene glycol groups are preferably used, e.g. 1 to 20 or 2 to 10.

The photoreactive monomers additionally have at least one photoreactive group, the photoreactive group preferably being a photoenolizable carbonyl group. A photoenolizable carbonyl group is a keto group or aldehyde group which can be converted into the respective enol tautomer by exposure to light. In the following, such compounds are also denoted for brevity as "photoenols".

Preferred photoenolizable carbonyl groups are photoenolizable alpha-arylcarbonyl groups. Suitable examples are compounds in which the photoreactive group is derived from a structural unit of the formula

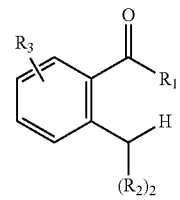

where $R_1$ is hydrogen or an organic residue, e.g. an alkyl group or aryl group, $R_2$ is hydrogen or an organic residue, e.g. an alkyl group, preferably methyl, and $R_3$ stands for the substituents on the aromatic ring which are identical or different from one another and may be linked to one another via one or more ring systems, e.g. hydrogen, alkyl groups or aryl groups.

In terms of the invention, an alkyl group is understood to mean preferably a $C_1$-$C_{20}$-alkyl residue.

The latter are straight-chain or branched hydrocarbon residues with up to 20 carbon atoms, preferably $C_1$-$C_{10}$-alkyl such as methyl, ethyl, propyl, isopropyl, n-butyl, sec-butyl, tent-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, 2,4,4-trimethylpentyl, 1,1,3,3-tetramethylbutyl, nonyl and decyl and also their isomers.

In terms of the invention an aryl group is a mono- to trinuclear aromatic ring system comprising 6 to 14 carbon ring members, e.g. phenyl, naphthyl and anthracenyl, preferably a mono- to bi-nuclear aromatic ring system, particularly preferably a mononuclear aromatic ring system.

Preferred photoreactive monomers are compounds having the structural formula (I)

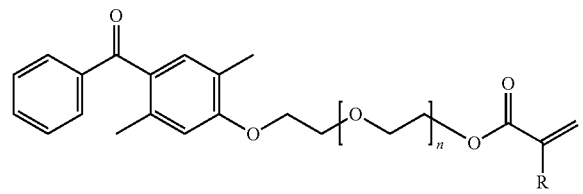

where n is a number from 0 to 29, preferably from 3 to 19, and R is hydrogen or methyl.

Preferred photoreactive monomers are also compounds having the structural formula (II)

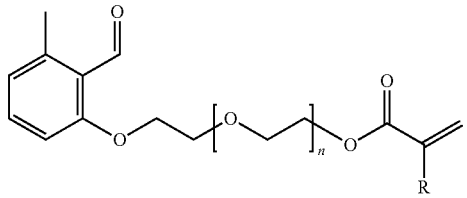

where n is a number from 0 to 19, preferably from 1 to 9, and R is hydrogen or methyl.

The invention likewise provides a method for preparing the photoreactive compounds.

In principle, the catalytic ethoxylation of photoreactive groups such as 4-hydroxy-2,5-dimethylphenylphenylmethanone is feasible, although it proceeds with poor yields, since the reactivity of the reactant is far below that of the ethoxylated product.

Therefore, compounds of formula (I), preferably starting from an ethylene glycol with the number of ethylene glycol groups corresponding to n=0 to 29, are reacted with p-toluenesulfonyl chloride. This is followed by reaction with a compound comprising a photoreactive group, in which this photoreactive group is a photoenolizable carbonyl group as described above. In the subsequent reaction, the free-radically polymerizable C—C double bond is inserted by reaction with a (meth)acryloyl halide, preferably a (meth)acryloyl chloride. Alternatively, the latter step can also effect acid esterification with (meth)acrylic acid according to known methods, in which suitable catalysts are, for example, acidic ion exchangers or, more favourably, p-toluenesulfonic acid, methanesulfonic acid and $H_2SO_4$. As an alternative to this, enzymatic catalysts such as, for example, a lipase from *Candida Antarctica* B are also suitable, these being commercially available under the name Novozym 435. Also of good suitability is the transesterification of (meth)acrylates using Lewis acids such as dibutyltin oxide, or titanium tetraisopropoxide, or with inorganic salts such as alkali metal or alkaline earth metal carbonates, bicarbonates, phosphates, hydrogen phosphates, dihydrogen phosphates, sulfates or sulfites. Preferred inorganic salts for a transesterification reaction are $Li_3PO_4$, $K_3PO_4$, $Na_3PO_4$, $K_2CO_3$ and $Na_2CO_3$.

Compounds of formula (II) are preferably prepared starting from a poly(ethylene glycol) (meth)acrylate, i.e. this starting material already comprises the hydrophilic group and the free-radically polymerizable C—C double bond. Then, for introduction of the photoreactive group, this reactant is firstly reacted with p-toluenesulfonyl chloride and subsequently with a compound comprising a photoreactive group, this photoreactive group being a photoenolizable carbonyl group as described above.

The syntheses of the compounds of formulae (I) and (II) are however in principle interchangeable.

The photoreactive groups which form the basis of the compounds of formula (I) can be prepared as described in the literature by a Fries rearrangement from simple starting components (C. Barner-Kowollik, Macromol. Rapid Commun. 32 (11), 807 2011 (supporting information)). A possible preparation via catalytic processes is found in DE 69321830. The preparation of the photoreactive groups of the compounds of formula (II) is described in C. Barner-Kowollik, Angew. Chem Int. Ed. 51, 1071, 2012, supporting information.

The photoreactive monomers may be used for preparing aqueous polymer dispersions or solutions which are employed in the film-forming products sector (adhesives, coatings, dyes and lacquers). These polymers can increase the stability of the films by the action of light and a high temperature is not required. They have potential applications in aqueous emulsion polymers for various purposes for modifying the particle surfaces or the films formed thereon. Products could be, for example, adhesives, in which their adhesive strength is reinforced by irradiation with light. Further products could be dyes or lacquers which have a superior abrasion resistance following light irradiation and are insoluble in water.

EXAMPLES

Example 1

Synthesis of Photoenol Monomer 1

Synthetic Scheme:
Synthesis of Tos-PEG-OH (1):
Tetraethylene glycol (15 g, 77.2 mmol) is dissolved in 220 mL of acetonitrile. Triethylamine is added dropwise under nitrogen. A solution of p-toluenesulfonyl chloride (14.718 g, 77.2 mmol) in 75 mL of acetonitrile is then added dropwise at 0° C. After stirring for 12 h at room temperature, the mixture is filtered and the solvent removed under reduced pressure. Purification by flash chromatography (silica gel, chloroform+10% methanol, Rf=0.68) gives a yellow oil (yield: 31%).

$^1$H-NMR (CDCl$_3$, 250 MHz): δ/ppm: 2.37 (s, 3H, CH$_3$), 2.68 (bs, 1H, OH), 3.50-3.65 (m, 14H, CH$_2$O), 4.09 (t, 2H, CH$_2$O), 7.29 (d, 2H, H$_{ar}$), 7.70 (d, 2H, H$_{ar}$).

Synthesis of PE-PEG-OH (2):
4-Hydroxy-2,5-dimethylphenylphenylmethanone (16.956 g, 74.9 mmol) is dissolved in 140 mL of anhydrous acetone under nitrogen. K$_2$CO$_3$ (10.352 g, 749 mmol) is then added. A solution of (1) (15.358 g, 44.1 mmol) in 40 mL of anhydrous acetone is added dropwise at room temperature. The mixture is heated under reflux for 39 h at 60° C. After cooling to room temperature, the mixture is filtered and the solvent removed under reduced pressure. Purification by flash chromatography (silica gel, Et$_2$O+10% methanol, Rf=0.53) gives a pale yellow oil (yield: 61%).

$^1$H-NMR (CDCl$_3$, 250 MHz): δ/ppm: 2.10 (s, 3H, CH$_3$), 2.29 (s, 3H, CH$_3$), 2.42 (bs, 1H, OH), 3.51-3.71 (m, 12H, CH$_2$O), 3.83 (t, 2H, CH$_2$O), 4.13 (t, 2H, CH$_2$O), 6.65 (s, 1H, H$_{ar}$), 7.08 (s, 1H, H$_{ar}$), 7.33-7.40 (m, 2H, H$_{ar}$), 7.45-7.51 (m, 1H, H$_{ar}$), 7.67-7.71 (m 2H, H$_{ar}$).

Synthesis of PE-PEG-acrylate (3):
Acryloyl chloride (1 mL, 12.4 mmol) is dissolved in 10 mL of anhydrous dichloromethane under nitrogen. A solution of (2) (2 g, 4.97 mmol) and triethylamine (2.08 mL, 14.9 mmol) in 15 mL of anhydrous dichloromethane is added dropwise at 0° C. After the addition, the mixture is allowed to warm to room temperature and stirred for 24 h. The solution is washed with water (2×25 mL) and brine (2×25 mL) and dried over MgSO$_4$. The solvent is removed under reduced pressure. Purification by flash chromatography (silica gel, Et$_2$O+5% methanol, Rf=0.80) gives a pale yellow oil (yield: 72%).

$^1$H-NMR (CDCl$_3$, 250 MHz): δ/ppm: 2.10 (s, 3H, CH$_3$), 2.30 (s, 3H, CH$_3$), 3.61-3.72 (m, 10H, CH$_2$O), 3.84 (t, 2H, CH$_2$O), 4.13 (t, 2H, CH$_2$O), 4.25 (t, 2H, CH$_2$O), 5.76 (dd, 1H, CH), 6.08 (dd, 1H, CH), 6.36 (dd, 1H, CH), 6.64 (s, 1H, $H_{ar}$), 7.08 (s, 1H, $H_{ar}$), 7.35-7.41 (m, 2H, $H_{ar}$), 7.46-7.52 (m, 1 H, $H_{ar}$), 7.67-7.71 (m 2H, $H_{ar}$).

Example 2

Synthesis of Photoenol Monomer 2

Synthetic Scheme:
Synthesis of Compound (6):

The synthesis is described for n=4-5; for n=9 the same preparation method can be used. Triethylamine (4.28 mL, 30.7 mmol) is added under nitrogen to a solution of poly(ethylene glycol) methacrylate (Mn=360, 11.05 g, 30.7 mmol) in 100 mL of acetonitrile. p-Toluenesulfonyl chloride (5.852 g, 30.7 mmol) is dissolved in 50 mL of acetonitrile and added dropwise at 0° C. After the addition, the mixture is allowed to warm to room temperature and stirred for 12 h. The solution is filtered and, following addition of hydroquinone (0.3 g), the solvent is removed under reduced pressure at 25° C. The crude product is used further without further purification.

Synthesis of Compound (7):
4-Hydroxy-2,5-dimethylphenylphenylmethanone (0.7976 g, 3.53 mmol) is dissolved in 15 mL of anhydrous acetone. Hydroquinone (0.1 g) and $K_2CO_3$ (0.69 g, 4.99 mmol) are added. After dropwise addition of a solution of (6) (n=9, 2.0 g, 2.94 mmol) in 25 mL of anhydrous acetone at room temperature, the mixture is heated under reflux for 22 h at 60° C. The solvent is removed under reduced pressure to form a dark brown oil.

Synthesis of Compound (8):
2-Hydroxy-6-methylbenzaldehyde (photoenol 2, 2.0 g, 14.7 mmol) is dissolved in 40 mL of anhydrous acetone. Hydroquinone (0.1 g) and $K_2CO_3$ (3.385 g, 24.5 mmol) are added. After drop-wise addition of a solution of (6) (n=4-5, 6.273 g, 12.2 mmol) in 30 mL of anhydrous acetone at room temperature, the mixture is heated under reflux for 18 h at 60° C. The solvent is removed under reduced pressure to form a dark brown oil.

The invention claimed is:

1. A photoreactive monomer represented by formula (II):

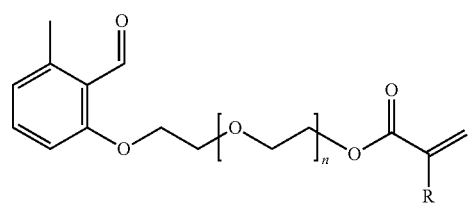

wherein
n is a number from 0 to 19 and
R is hydrogen or methyl.

2. The photoreactive monomer of claim 1, wherein n is 1 to 9.

3. The photoreactive monomer of claim 1, wherein R is hydrogen.

4. The photoreactive monomer of claim 1, wherein R is methyl.

* * * * *